United States Patent

Belfer

[11] Patent Number: 5,720,302
[45] Date of Patent: Feb. 24, 1998

[54] ANTI-SNORING DEVICE HAVING AN EXTERNAL SHIELD

[76] Inventor: William A. Belfer, 804 W. Park Ave., Ocean Township, N.J. 07712

[21] Appl. No.: 609,617

[22] Filed: Mar. 1, 1996

[51] Int. Cl.⁶ .................................................. A61F 5/56
[52] U.S. Cl. ........................... 128/848; 128/859; 602/902
[58] Field of Search ................................. 128/846, 848, 128/859–862; 2/2; 602/902

[56] References Cited

U.S. PATENT DOCUMENTS

| | | |
|---|---|---|
| 1,674,336 | 6/1928 | King . |
| 2,178,128 | 10/1939 | Waite . |
| 3,692,025 | 9/1972 | Greenberg .............................. 128/861 |
| 4,169,473 | 10/1979 | Samelson . |
| 4,170,230 | 10/1979 | Nelson . |
| 4,198,967 | 4/1980 | Dror ....................................... 128/860 |
| 4,495,945 | 1/1985 | Liegner ............................. 128/200.26 |
| 4,676,240 | 6/1987 | Gardy . |
| 4,901,737 | 2/1990 | Toone . |
| 4,944,947 | 7/1990 | Newman ................................ 128/861 |
| 5,003,994 | 4/1991 | Cook . |
| 5,046,512 | 9/1991 | Murchie . |
| 5,092,346 | 3/1992 | Hays et al. . |
| 5,117,816 | 6/1992 | Shapiro .................................. 128/848 |
| 5,277,202 | 1/1994 | Hays . |
| 5,365,946 | 11/1994 | McMillan ............................... 128/861 |
| 5,467,783 | 11/1995 | Meade . |

*Primary Examiner*—Michael A. Brown
*Attorney, Agent, or Firm*—Ezra Sutton

[57] ABSTRACT

An anti-snoring device including a denture member for covering the lower teeth of the user and for maintaining the tongue in contact with the palate to prevent air flow from causing the palate to reverberate during mouth breathing; an extension member fixedly connected to the front of the denture member; and a flexible oral shield having an opening for slidably receiving the extension member and having at least one breathing hole. The flexible oral shield is worn outside the mouth and is conformable to the user's lips for preventing the lower jaw from drifting inferiorly and posteriorly during sleep.

7 Claims, 4 Drawing Sheets

ANTI-SNORING DEVICE HAVING AN EXTERNAL SHIELD

FIELD OF THE INVENTION

This invention relates to an anti-snoring device, and more particularly, to an anti-snoring device having an external oral shield which reduces air turbulence and promotes nasal breathing while sleeping to prevent the act of snoring.

BACKGROUND OF THE INVENTION

Snoring or sleep apnea is caused by the condition where the tongue relaxes and contributes to blocking of the air passageway in the pharynx or lingual compartment. Further, the loose tissue within the mouth cavity including the tongue, the pharyngeal folds, the soft palate, the muscularis uvulae and the palate-pharyngeal arch tend to vibrate as tidal air flows past during sleep which also causes snoring.

Anti-snoring devices are effective when they protract (pull or hold) the mandible (lower jaw) forward and upward and elevate the tongue, so that the tongue does not occlude the air passageway drifting inferiorly and posteriorly while sleeping. Most anti-snoring devices accomplish this aforementioned task by holding the lower jaw forward against a rigid dental component which is fixed to the upper teeth or to the upper and lower teeth. These anti-snoring devices fix the dental component from falling out of the mouth by clasping or biting of the user's teeth into the dental component and by close adaptation to the user's teeth. The primary disadvantages in using the above prior art devices, is that they require professional lab services for fitting of the anti-snoring device to the user's mouth. Such devices could cause irreversible changes in the bite of the user or permanently alter the jaw position of the user unless the anti-snoring device fitting is closely supervised by a dentist.

There is a need for an anti-snoring device that does not rigidly bind to the dental structures of the user's mouth and does not require professional supervision or assistance in its fabrication. In addition, the anti-snoring device should not pit the lower jaw against the upper jaw and should not alter the bite of the user. Further, an external oral shield should be used to hold the lower jaw from drifting inferiorly and posteriorly during sleep. The oral shield would be adjustable by the user, such that the device can be adjusted to fit various jaw sizes and bite relationships. Also, the device should include an intra oral dental overlay to support the tongue against the palate and keep the palate of the user's mouth from reverberating during mouth breathing.

DESCRIPTION OF THE PRIOR ART

Anti-snoring devices of various designs, appearances, styles and materials of construction have been disclosed in the prior art. For example, U.S. Pat. No. 2,178,128 to Waite discloses an anti-snoring device having a shield worn inside the mouth. This device does not have a contacting dental overlay. U.S. Pat. No. 4,169,473 to Samelson discloses an anti-snoring device having an oral shield, upper and lower dental overlays, and a tongue-receiving socket. This device is structurally and functionally different from the present invention.

The prior art patents do not teach or disclose the structure of the present invention of an anti-snoring device having an external, adjustable oral shield with breathing holes being worn outside the mouth, and which is removably connected by an anterior handle to a lower arch dental overlay for elevating the tongue. In addition, the prior art does not disclose an oral shield that is slidable relative to the dental overlay along the length of the anterior handle.

Accordingly, the primary object of the present invention is to provide an anti-snoring device having an external oral shield and a dental overlay connected by an anterior handle to reduce or eliminate nocturnal snoring.

Another object of the present invention is to provide an anti-snoring device that is easily self-adaptable and which eliminates the need for professional and laboratory assistance or clinical fabrication.

Another object of the present invention is to provide an anti-snoring device that is fabricated from a thermoplastic material (elastomeric resin) which is moldable in shape to the user's lower jaw and perioral structure.

Another object of the present invention is to provide an anti-snoring device which is moldable after immersion in boiling water so that it can be adapted by the user to have a comfortable and individualized fit.

Another object of the present invention is to provide an anti-snoring device that has an external oral shield structure which reduces air turbulence within the user's mouth and thus promotes nasal breathing to prevent the act of snoring.

Another object of the present invention is to provide an anti-snoring device that has an external oral shield structure which acts a lip seal, such that the user is more apt to breath through the nose instead of the mouth to prevent the act of snoring.

Another object of the present invention is to provide an anti-snoring device that has an intra oral dental overlay structure which supports the tongue against the user's palate to keep the palate from reverberating during mouth breathing to prevent snoring by the user.

Another object of the present invention is to provide an anti-snoring device that includes an external oral shield in combination with an intraoral dental overlay connected by an anterior handle, such that the oral shield can be slidably adjusted on the handle by the user and which reduces the velocity of air flow through the mouth to reduce the reverberation of the palate to prevent the act of snoring.

A further object of the present invention is to provide an anti-snoring device which can be easily used, mass produced in an automated and economical manner, and is readily affordable by the user.

A still further object of the present invention is to provide an adjustability of the oral shield along the handle of the dental overlay, which will allow the device to accommodate individual differences in the upper and lower jaw relationships of users. The user is able to adjust the entire anti-snoring device comfortably without sophisticated procedures and professional help.

SUMMARY OF THE INVENTION

In accordance with the present invention, there is provided an new and improved anti-snoring device for controlling snoring during sleep. The anti-snoring device includes a dental overlay member for covering the lower teeth of the user and for maintaining the tongue in contact with the palate to prevent air flow from causing the palate to reverberate during mouth breathing; an anterior handle member fixedly connected to the front of the dental overlay; and a flexible oral shield having an opening for slidably receiving the anterior handle member and having at least one breathing hole. The flexible oral shield is worn outside the mouth and is conformable to the user's lips for preventing the lower jaw from drifting inferiorly and posteriorly during sleep to prevent snoring. The anti-snoring device may be made of thermoplastic or elastomeric resin materials for moldability to the user's mouth.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

Figure 1:
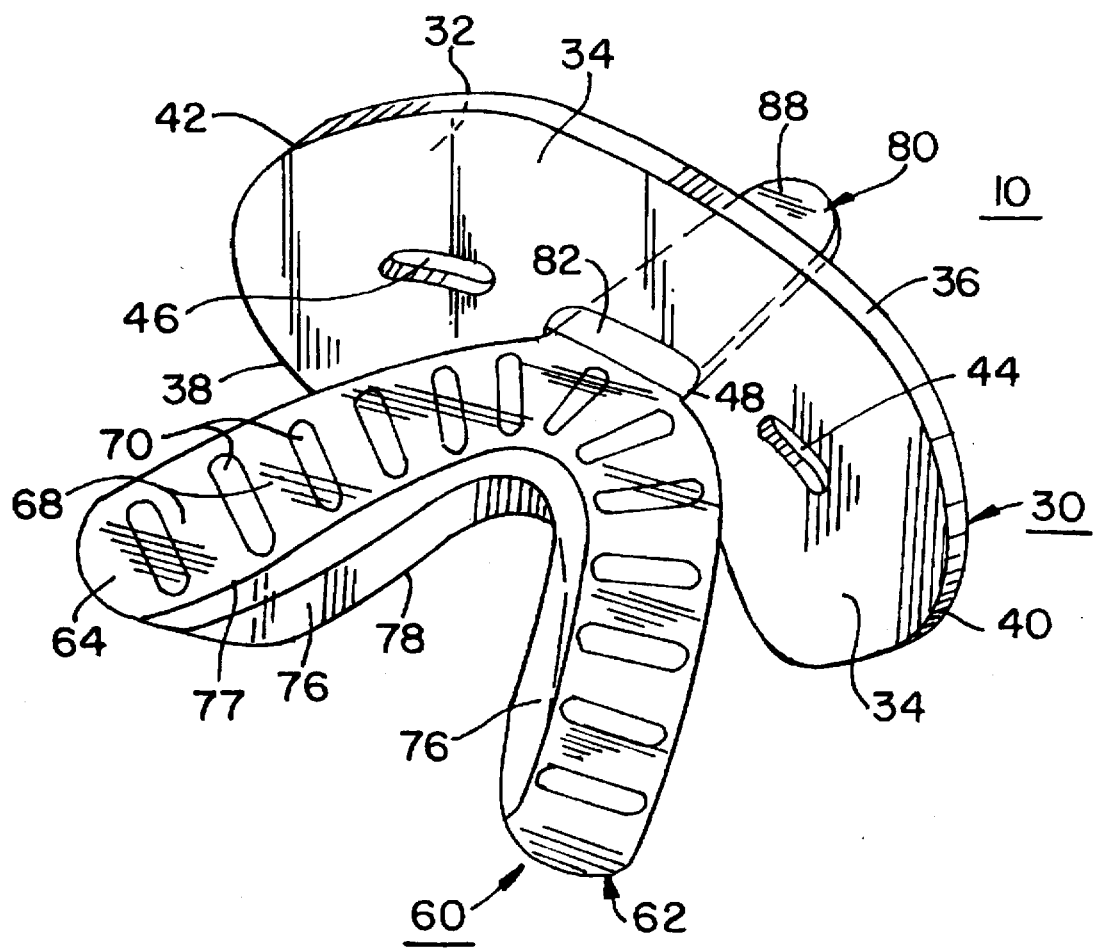
FIG. 1 is a perspective view of the preferred embodiment of the present invention showing an anti-snoring device having an external oral shield and an intraoral dental overlay with an anterior handle attached thereto.

The anti-snoring device 10 and its component parts of the preferred embodiment of the present invention are represented in detail by FIGS. 1 through 4. The anti-snoring device 10 comprises an external, adjustable oral shield 30 being substantially elliptical and convex in shape; and an intraoral lower dental overlay 60 having an integrally attached anterior handle 80, as shown in FIG. 1. The oral shield 30 and dental overlay 60 are made from a flexible thermoplastic material (elastomeric resin) which are moldable after immersion in boiling water; such that the user may mold the oral shield 30 and dental overlay 60 to the shape of his or her lower jaw 12, perioral area 26 and lip area 28. Such moldable materials of construction may include ethyl vinyl acetate, methyl vinyl acetate, methyl acrylate, or other elastic resins which are softened and moldable in hot water and return to a hardened and stable form upon cooling to room temperature. The oral shield 30, dental overlay 60, and anterior handle 80 may be formed by an injection molding process.

Figure 2:
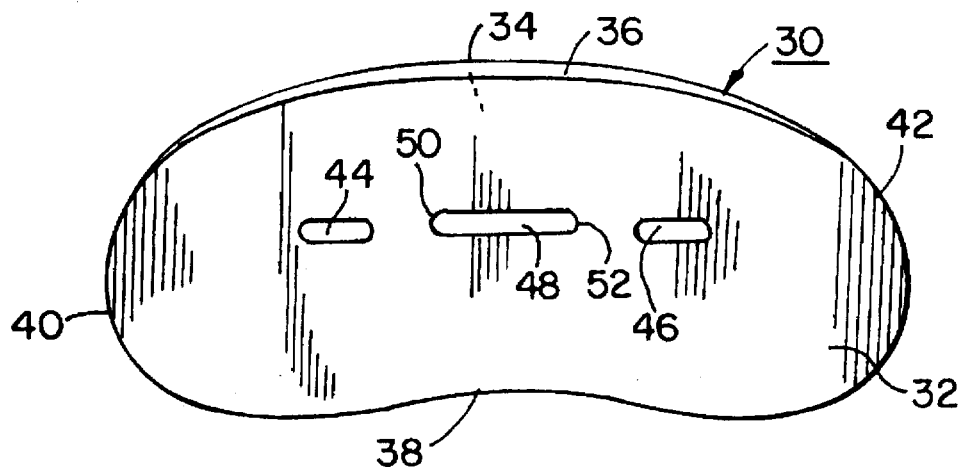
FIG. 2 is a front perspective view of the present invention showing the external oral shield having two breathing hole openings and a center handle slot opening.

Oral shield 30, as shown in FIGS. 1 and 2, includes an outer surface wall 32, and an inner surface wall 34 having upper, lower and side perimeter edges 36, 38, 40, and 42. In addition, oral shield 30 further includes two elliptical shaped breathing hole openings 44 and 46 for mouth breathing 26; and elongated oval handle slot opening 48 for slidably receiving anterior handle 80 of dental overlay 60. Handle slot opening 48 is centrally located within oral shield 30 and breathing hole openings 44 and 46 are in-line and adjacent to each side 50 and 52 of handle slot opening 48.

Figure 3:
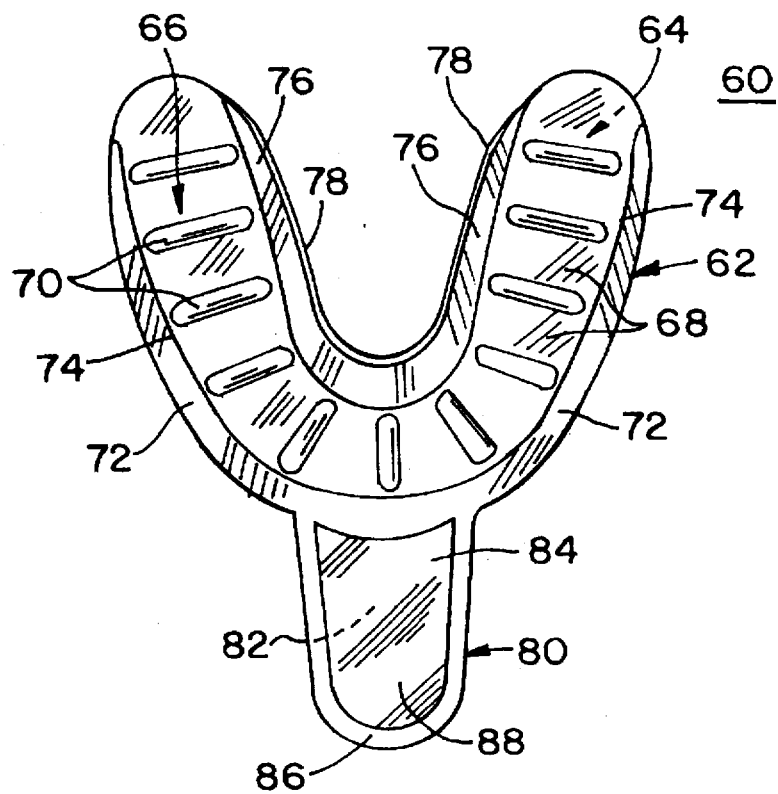
FIG. 3 is a rear, bottom perspective view of the present invention showing the intraoral dental overlay having an integrally attached anterior handle for inserting into the handle slot opening of the oral shield.

The intraoral dental overlay 60 has a housing 62 which is substantially U-shaped in cross section and has an integrally attached anterior handle 80 located at the bottom-end of U-shaped housing 62, as shown in FIGS. 1 and 3. Dental overlay 60 includes outer surface wall 64, and inner surface wall 66 having an integrally attached outer perimeter wall 72 with an outer perimeter edge 74 and an integrally attached inner perimeter wall 76 with an inner upper and lower perimeter edges 77 and 78. The inner surface wall 66 is molded into a plurality of spaced-apart tooth- receiving areas 68 separated by occlusal ribs 70. The inner perimeter wall 76 and the inner upper perimeter edge 77 acts as the lingual shelf portion of the dental overlay 60. The inner wall 76, is thicker than the outer wall 72 and the inner wall 76,has a greater depth than the outer wall 72, the inner wall 76 also forms a part of a lingual shelf for supporting the tongue in contact with the palate. It is the lingual shelf portion which acts as a support for the tongue 16 against the palate 18 of the mouth 26 of the user. The lingual shelf portion helps to prevent the act of snoring.

The anterior handle 80 includes an elongated strip 88 formed of plastic having top and bottom surfaces 82 and 84 and a U-shaped perimeter edge 86. The oral shield 30 may be slidably adjusted on strip section 88 of anterior handle 80 by the user.

In an alternate embodiment, an upper dental overlay component can be attached to outer surface wall 66 of the lower dental overlay component to form a unitary construction for covering the upper and lower teeth. The tongue is received in the open space formed by the upper and lower dental overlay components.

OPERATION OF THE PRESENT INVENTION

The anti-snoring device 10 of the present invention is designed and fabricated to be molded by the user without any assistance by a professional or a clinical laboratory. The initial step begins with the user immersing the dental overlay 60 and oral shield 30 into a container of boiling water. The dental overlay 60 and oral shield 30 are then moldable after immersion in boiling water, such that the aforementioned components 30 and 60 can be fitted by the user to give a comfortable and individualized fit. The molding act is performed by the user, simply inserting the dental overlay 60 into the mouth 26, and placing the dental overlay 60 on the lower teeth 22 of lower jaw 12. The user then moves his/her jaw 12, lips 28, and tongue 16 around; and bites with lower teeth 22 into the inner surface wall 66 of the softened elastomeric material which forms the dental overlay 60 to the individualized shape of the user's lower jaw area 12.

The next molding step is then effected by immersing the oral shield 30 in boiling water which allows this elastomeric component to become softened. The oral shield 30 is then taken out of the hot water and allowed to cool slightly before the user presses the oral shield 30 against his/or her lips 28 and perioral mouth tissues 26. The oral shield 30 is thus individualized to the users lips 28 and mouth area 26 and the oral shield 30 is then fitted onto the anterior handle 80 of the dental overlay 60 and slid along the handle strip 88 via the handle slot opening 48 until the oral shield 30 meets the users lips 28. The anti-snoring device 10 is now ready for use to prevent snoring while sleeping.

Figure 5:
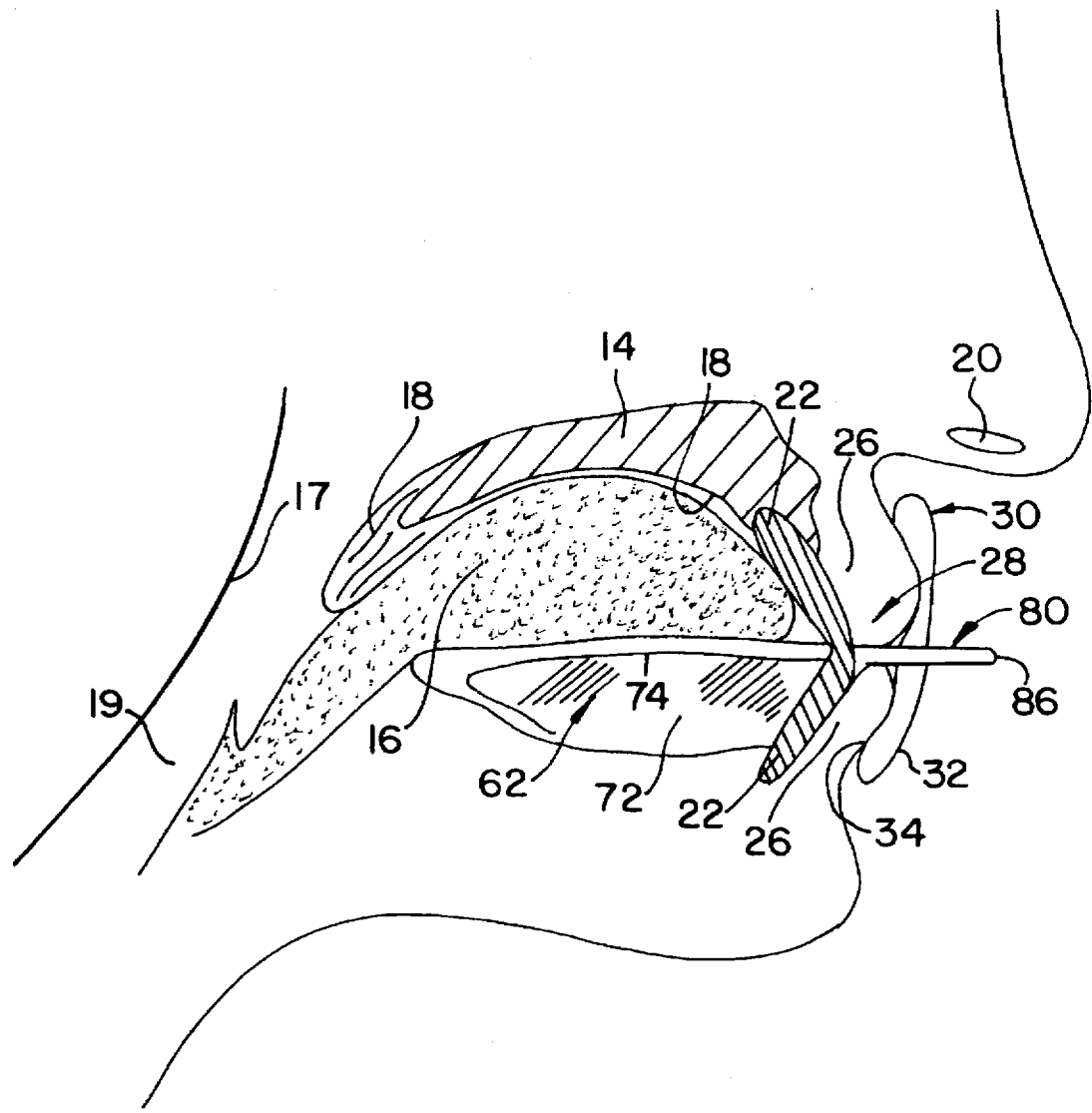
FIG. 5 is a cross-sectional view of the present invention showing the anti-snoring device in an operational mode and with the device inserted in the oral cavity having the user's tongue elevated to prevent snoring by a user.

When the user is ready to sleep the anti-snoring device 10 is kept fully assembled. The dental overlay 60 is then inserted into the user's mouth 26 and placed on the lower teeth 22. The final act of adjustment occurs when the user slides the oral shield 30 towards the lips 28 and at the same time the user postures the mandible (lower jaw) 12 forward. In so doing the tongue 16 is also postured forward, as depicted in FIG. 5 of the drawings. This posturing act carries the tongue 16 forward and away from the posterior wall 17 of the pharynx 19 which enables unobstructed respiration.

Figure 4:
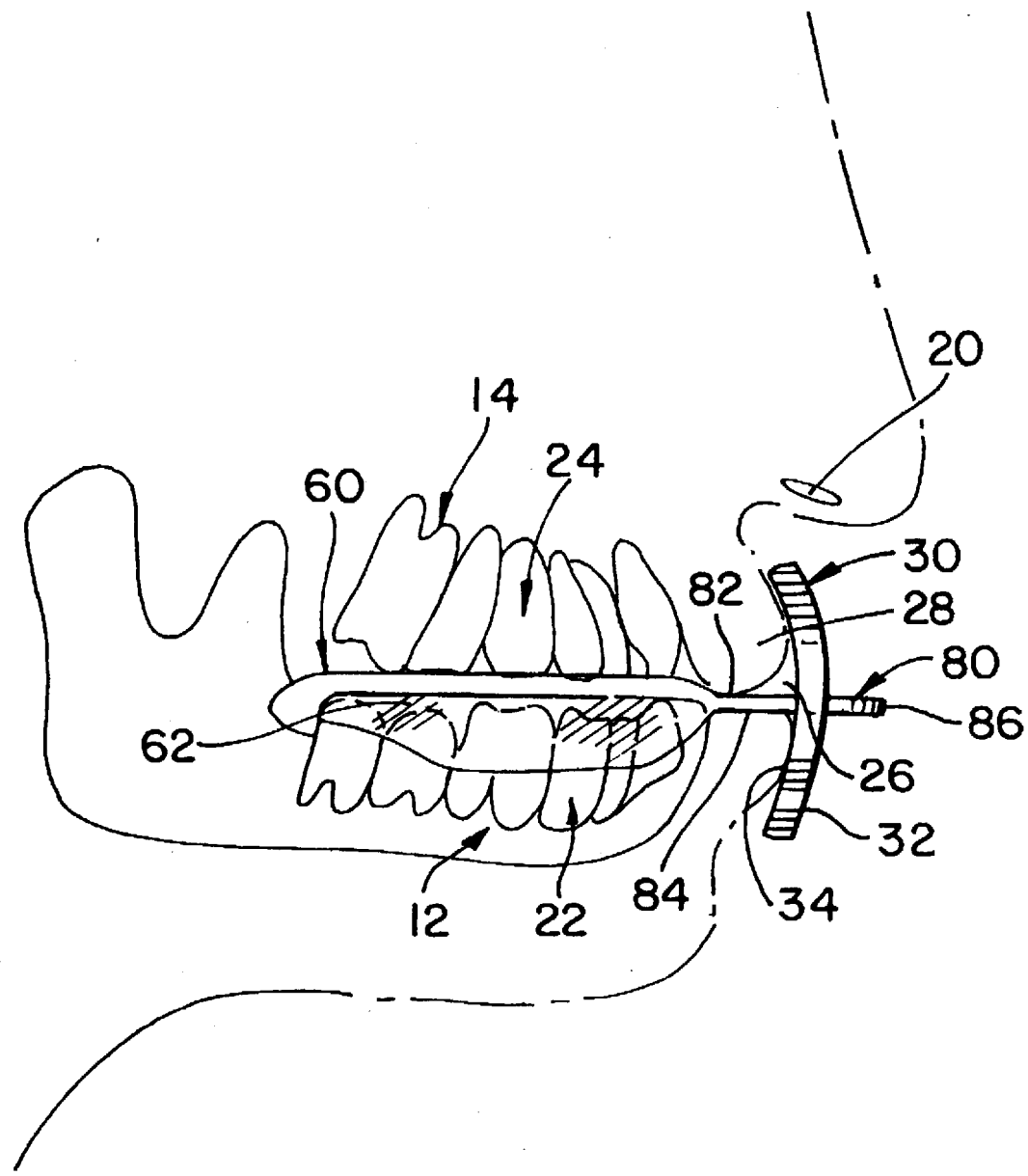
FIG. 4 is a cross-sectional view of the present invention showing the anti-snoring device inserted in the oral cavity of a user.

Furthermore, the oral shield 30 acts as a lip seal so that the user is more apt to breath through the nasal passages 20 instead of the mouth 26, as shown in FIGS. 4 and 5. Once the anti-snoring device 10 is properly in place the user can sleep comfortably without any interference from the device 10 while sleeping. During sleep the dental overlay 60 supports the tongue and keeps it in engagement with the palate to reduce the reverberation of the palate which causes snoring.

ADVANTAGES OF THE PRESENT INVENTION

Accordingly, the featured advantage of the present invention is that it provides for an anti-snoring device having an external oral shield and a dental overlay connected by an anterior handle to reduce or eliminate nocturnal snoring.

Another advantage of the present invention is that it provides for an anti-snoring device that is easily self-adaptable and which eliminates the need for professional and laboratory assistance or clinical fabrication.

Another advantage of the present invention is that it provides for an anti-snoring device that is fabricated from a thermoplastic material (elastomeric resin) which is moldable in shape to the user's lower jaw and perioral structure.

Another advantage of the present invention is that it provides for an anti-snoring device which is moldable after immersion in boiling water so that it can be adapted by the user to have a comfortable and individualized fit.

Another advantage of the present invention is that it provides for an anti-snoring device that has an external oral shield structure which reduces air turbulence within the user's mouth and thus promotes nasal breathing to prevent the act of snoring.

Another advantage of the present invention is that it provides for an anti-snoring device that has an external oral shield structure which acts a lip seal, such that the user is more apt to breath through the nose instead of the mouth to prevent the act of snoring.

Another advantage of the present invention is that it provides for an anti-snoring device that has an intra oral dental overlay structure which supports the tongue against the user's palate to keep the palate from reverberating during mouth breathing to prevent snoring by the user.

Another advantage of the present invention is that it provides for an anti-snoring device that includes an external oral shield in combination with an intraoral dental overlay connected by an anterior handle, such that the oral shield can be slidably adjusted on the handle by the user and which reduces the velocity of air flow through the mouth to reduce the reverberation of the palate to prevent the act of snoring.

A further advantage of the present invention is that it provides for an anti-snoring device which can be easily used, mass produced in an automated and economical manner, and is readily affordable by the user.

A still further advantage of the present invention is that it provides for adjustability of the oral shield along the handle of the dental overlay and allows the device to accommodate individual differences in the upper and lower jaw relationships of users. The user is able to adjust the entire anti-snoring device comfortably without sophisticated procedures and professional help.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. An anti-snoring device comprising:
   a) a moldable dental overlay for covering only the lower teeth of the user and for maintaining the tongue in contact with the palate to prevent air flow from causing the palate to reverberate during mouth breathing; said dental overlay having an inner wall forming a part of a lingual shelf for supporting the tongue in contact with the palate;
   b) an extension member fixedly connected to the front 6f said dental overlay; and
   c) a moldable oral shield having an opening for slidably receiving said extension member; said oral shield being movable along said extension member to come in contact with said dental overlay; said shield having at least one breathing hole; said oral shield worn outside the mouth and being conformable to the user's lips for preventing the lower jaw from drifting interiorly and posteriorly during sleep, wherein said dental overlay has an inner wall thicker than said outer wall, and said inner wall has a greater depth than said outer wall, said inner wall forming a part of a lingual shelf for supporting the tongue in contact with the palate.

2. An anti-snoring device in accordance with claim 1, wherein said anti-snoring device is made of moldable thermoplastic or elastomeric resin materials.

3. An anti-snoring device in accordance with claim 2, wherein said thermoplastic or elastomeric resin materials are selected from the group consisting of ethyl vinyl acetate, methyl vinyl acetate, or methyl acrylate.

4. An anti-snoring device in accordance with claim 1, wherein said oral shield has two or more breathing holes.

5. An anti-snoring device in accordance with claim 1, wherein said dental overlay has a plurality of teeth receiving areas separated by adjacent occlusal ribs.

6. An anti-snoring device in accordance with claim 1, wherein said dental overlay covers all lower teeth.

7. An anti-snoring device in accordance with claim 1, wherein said extension member is a flexible strip of plastic.

* * * * *